US010617406B2

(12) United States Patent
Housman et al.

(10) Patent No.: US 10,617,406 B2
(45) Date of Patent: Apr. 14, 2020

(54) SUTURE ANCHOR SYSTEM WITH THREADED PLUG

(71) Applicant: Smith & Nephew, Inc., Memphis, TN (US)

(72) Inventors: Mark Edwin Housman, North Attleboro, MA (US); Nehal Navinbhai Patel, Boston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 172 days.

(21) Appl. No.: 15/738,329

(22) PCT Filed: Jun. 30, 2015

(86) PCT No.: PCT/US2015/038460
§ 371 (c)(1),
(2) Date: Dec. 20, 2017

(87) PCT Pub. No.: WO2017/003442
PCT Pub. Date: Jan. 5, 2017

(65) Prior Publication Data
US 2018/0161026 A1 Jun. 14, 2018

(51) Int. Cl.
*A61B 17/04* (2006.01)
(52) U.S. Cl.
CPC .. *A61B 17/0401* (2013.01); *A61B 2017/0409* (2013.01); *A61B 2017/0412* (2013.01);
(Continued)
(58) Field of Classification Search
CPC ............ A61B 17/0401; A61B 17/0409; A61B 17/0412; A61B 2017/0414;
(Continued)

(56) References Cited

U.S. PATENT DOCUMENTS

| 2003/0065390 A1* | 4/2003 | Justin ................... A61F 2/0811 623/13.14 |
| 2009/0112270 A1* | 4/2009 | Lunn .................. A61B 17/0401 606/301 |

(Continued)

FOREIGN PATENT DOCUMENTS

| WO | 2011059995 A2 | 5/2011 |
| WO | 2011060022 A2 | 5/2011 |

OTHER PUBLICATIONS

ISR/WO for PCT application No. PCT/US2015/038460 dated Sep. 18, 2015.
(Continued)

*Primary Examiner* — Jocelin C Tanner
(74) *Attorney, Agent, or Firm* — Norman F. Hainer, Jr.

(57) ABSTRACT

A suture anchor system including an anchor, a plug and an inserter. The anchor inserter includes a tubular outer shaft having a cannulation dimensioned to receive an inner shaft. The distal end of the outer shaft cannulation is threaded for engagement with the plug. The anchor includes a longitudinal cannulation formed within the anchor body, including a smooth-sided portion and a threaded portion. An eyelet, dimensioned to receive a suture therein, extends transverse to the longitudinal axis of the anchor and intersects the distal portion of the cannulation. The plug is a generally elongated, tubular threaded rod comprising a cannulation adapted to receive a distal end of the inner inserter shaft.

20 Claims, 4 Drawing Sheets

(52) U.S. Cl.
CPC ............... *A61B 2017/0414* (2013.01); *A61B 2017/0445* (2013.01); *A61B 2017/0453* (2013.01)

(58) Field of Classification Search
CPC .... A61B 2017/0445; A61B 2017/0453; A61B 2017/0422; A61B 2017/0433; A61B 2017/044; A61B 2017/0446; A61B 2017/0448; A61B 2017/045
See application file for complete search history.

(56) References Cited

U.S. PATENT DOCUMENTS

2011/0112576 A1* 5/2011 Nguyen ............. A61B 17/0401
606/232
2014/0364906 A1 12/2014 Palese et al.

OTHER PUBLICATIONS

Japanese Application No. 2017-562025 Notice of Reasons for Rejection dated Jan. 11, 2019.

* cited by examiner

SUTURE ANCHOR SYSTEM WITH THREADED PLUG

CROSS-REFERENCE TO RELATED APPLICATIONS

This application is the U.S. national phase entry under 35 U.S.C. § 371 of International Application No. PCT/US2015/038460, filed Jun. 30, 2015, entitled "SUTURE ANCHOR SYSTEM WITH THREADED PLUG."

BACKGROUND

Arthroscopy surgery is a minimally-invasive surgery that involves the repair of tissue inside or around a joint. In shoulder arthroscopy, for example, common injuries include a torn or damaged cartilage ring or ligaments (causing shoulder instability), a torn rotator cuff, or a torn or damaged biceps tendon. Each of these injuries necessitates the reattachment of soft tissue (that is, the ligaments or tendons) to bone.

Suture anchors and suture anchor systems are useful fixation devices for fixing tendons and ligaments to bone. A typical suture anchor is inserted into the bone by pounding the suture anchor into the bone or by way of a bone hole using an anchor inserter. The suture anchor can be configured as a screw mechanism or an interference fit device and may be made of metal, plastic or bioabsorbable material (which dissolves in the body over time). The suture anchor can include an eyelet that allows one or more sutures to pass therethrough and link the suture anchor and the suture.

During the anchor insertion process, it is difficult for a surgeon to achieve linear stability of the suture anchor while it is coupled to a mating, disposable inserter. Currently, an additional suture which is wrapped through the anchor and cleated to the inserter handle is often used to achieve linear stability. This method creates an additional strand of suture which can gets in a surgeon's way during a procedure. Other suture anchors are couple to inserters with press fits or other suture constructs which also may cause obstruction.

SUMMARY

Accordingly, there is a need for a suture anchor system and method to fix an anchor to an inserter before insertion into bone, and to release the anchor from the inserter after completion, without adding additional steps for the surgeon. Additional advantages of such a system would be superior fixation force, and a streamlined design that would be more cost-effective to manufacture than current suture anchor systems.

Described herein is a suture anchor system including an anchor inserter, a corresponding suture anchor, and a plug adapted for transfer from the anchor inserter to the anchor.

In one example, a suture anchor system of this disclosure can include: 1) an inserter having an elongated, cannulated outer shaft extending between a proximal end and a distal end, a distal end of the outer shaft being threaded; 2) an anchor having an elongated anchor body extending longitudinally between a proximal end and a distal end, a closed eyelet, extending transversely through a longitudinal axis of the anchor, and dimensioned to receive one or more sutures, and a cannulation formed within the anchor body and intersecting the eyelet, the cannulation including a proximal cannulation portion extending distally from the proximal end of the anchor body to a first longitudinal position proximal to the eyelet, and a threaded distal cannulation portion extending distally from the first longitudinal position to a second longitudinal position distal to the eyelet; and 3) a threaded, tubular plug having a longitudinal cannula extending between a proximal end and a distal end. The inner shaft of the inserter may be engageable with the cannula of the plug to move the plug distally with respect to the anchor from a first axial position to a second axial position. In the first axial position, the plug can engage both the anchor body and the outer shaft of the inserter and a distal terminus of the plug may be proximal to the eyelet. In the second axial position, the plug can engage the anchor body, but not the outer shaft of the inserter, and the distal terminus of the plug can abut a distal terminus of the anchor body cannulation. The inserter can be made of any type of metal. A diameter of the distal end of the inserter can be smaller than a diameter of the rest of the inserter. A size of the distal end of the inserter may be selected to couple with the proximal cannulation portion of the anchor. The anchor can be made of one of a plastic, a bioabsorbable material and/or a metal. The distal end of the anchor body may be closed. The proximal cannulation portion of the anchor can be non-threaded. Moving the plug distally with respect to the anchor may includes rotating the inner shaft of the inserter. The plug can be made of any one of a plastic, a bioabsorbable material and/or a metal. A plug length may be between about 5 mm and about 8.5 mm and a plug diameter may be between about 1.9 mm and about 2.1 mm.

In another example, a method of securing a suture of this disclosure can include: 1) routing a suture through an eyelet dimensioned to receive one or more sutures extending transversely through a longitudinal axis of an anchor, the anchor further having an elongated anchor body extending longitudinally between a proximal end and a distal end and a cannulation formed within the anchor body and intersecting the eyelet, the cannulation including a proximal cannulation portion extending distally from the proximal end of the anchor body to a first longitudinal position proximal to the eyelet, and a threaded distal cannulation portion extending distally from the first longitudinal position to a second longitudinal position distal to the eyelet; 2) engaging a distal end of a threaded, tubular plug with the distal cannulation portion of the anchor, the plug further having a longitudinal cannula extending between a proximal end and a distal end; 3) engaging a proximal end of the plug with a threaded distal end of a cannulation of an outer shaft of an inserter, the inserter further having an elongated inner shaft extending between a proximal end and a distal end, the inner shaft being dimensioned for receipt within and axially moveable independent of the outer shaft; 4) inserting the threaded distal end of the cannulation of the outer shaft of the inserter within the proximal cannulation portion of the anchor; and 5) engaging the inner shaft of the inserter with the cannula of the plug to move the plug distally with respect to the anchor from a first axial position, where the plug engages both the anchor body and the outer shaft of the inserter and a distal terminus of the plug is proximal to the eyelet, to a second axial position, where the plug engages the anchor body but not the outer shaft of the inserter and the distal terminus of the plug abuts a distal terminus of the anchor body cannulation, whereby the suture is secured between the distal terminus of the plug and the distal terminus of the anchor body cannulation. The method may further include removing the inserter from the anchor.

The advantages of this design is a streamlined device assembly in a neat, contained and reliable fashion, and may present cost benefits during manufacture. Furthermore, this form of fixation is far superior than other systems in terms of fixation force. Finally, the total number of steps in a surgical procedure is reduced, since there is no need to remove an extra suture.

For a better understanding of the present disclosure, together with other and further needs thereof, reference is made to the accompanying drawings and the following detailed description.

BRIEF DESCRIPTION OF THE DRAWINGS

The foregoing and other objects, features and advantages of the invention will be apparent from the following more particular description of the examples, as illustrated in the accompanying drawings, in which.

DETAILED DESCRIPTION

Figure 1A:
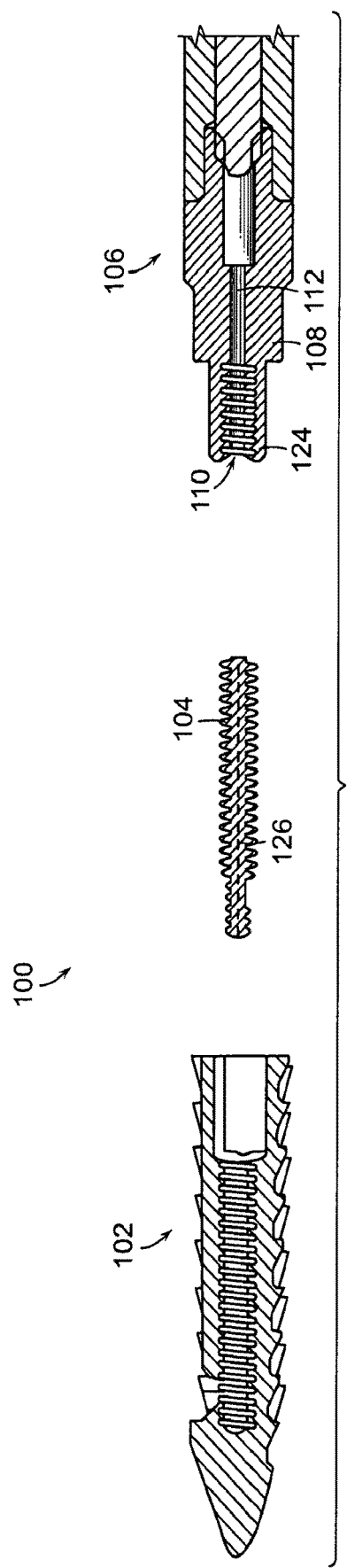
FIG. 1A is an exploded view of an example of the suture anchor system of this disclosure.

In the description that follows, like components have been given the same reference numerals, regardless of whether they are shown in different examples. To illustrate an example(s) of the present invention in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and in the claims, the singular form of "a", "an", and "the" include plural referents unless the context clearly dictates otherwise.

As used in the specification and in the claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue.

Referring now to FIG. 1A, an exploded, cross-sectional view of an example of the suture anchor system 100 of this disclosure is shown. The suture anchor system 100 generally includes a suture anchor 102, a threaded plug 104, and an inserter 106. The suture anchor 102 can have a solid, hard barb design, as shown in FIG. 1A, although other anchor designs are possible. The suture anchor 102 can also be a pound in device or a screw in device. The suture anchor 102 may be completely, or portions thereof, made from a formulation of poly(lactic-co-glycolic) acid (PLGA), β-Tricalcium phosphate (β-TCP) and calcium sulfate, poly-L-lactic acid-hydroxyapatite (PLLA-HA), poly-D-lactide (PDLA), polyether ether ketone (PEEK) or variants thereof. Biocomposite embodiments of the suture anchor made from a combination of PLGA, β-TCP, and calcium sulfate are absorbable by the body, which is beneficial to natural healing. An example formulation of PLGA, β-TCP, and calcium sulfate is described in U.S. Pat. No. 8,545,866, the entirety of which is herein incorporated by reference. Other commonly used material for suture anchors are also contemplated by this disclosure.

The threaded plug 104 of the suture anchor system 100 is substantially tubular and includes a cannula 126 extending from a proximal to a distal end. A plug length may be between about 5 mm and about 8.5 mm. A plug diameter may be between about 1.9 mm and about 2.1 mm. The plug 104 may be fully threaded about its surface or, as shown in FIG. 1A, may have a distal portion that is unthreaded. The plug 104 may be made of a plastic, metal, or bioabsorbable material. The distal end of the plug 104 may be open and in communication with the cannula 126 or may be closed-ended. The cannula 126 may extend distally through the entire length of the plug 104 or to any functional distance proximal thereto. The cannula 126 is dimensioned to receive an inner shaft 112 of the inserter 106, as further described below.

Figure 1B:
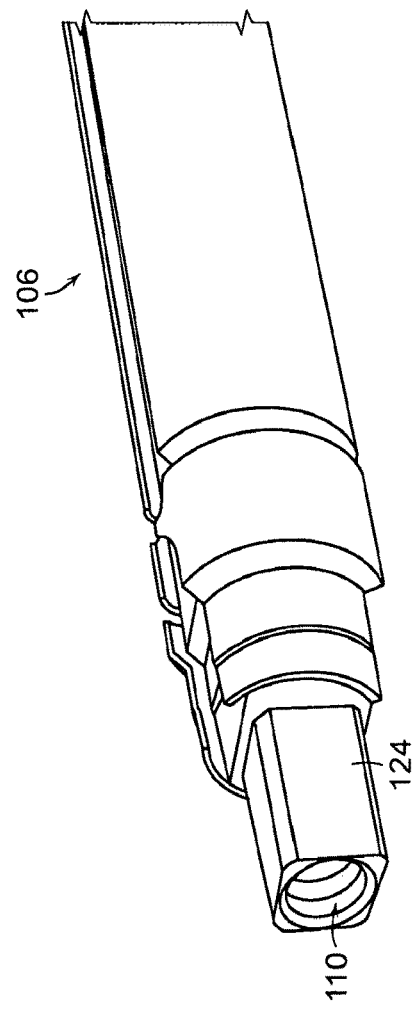
FIG. 1B is isometric view of an example of the inserter of FIG. 1A.

The inserter 106 of the suture anchor system 100 includes an elongated, cannulated outer shaft 108 extending between a proximal end and a distal end of the inserter 106. An inner surface of a distal end 124 of the outer shaft 108 further has threads 110 to engage the threads of the plug 104. A diameter of the distal end 124 is smaller than a diameter of any portion of the rest of the inserter 106, so that when the distal end of the outer shaft 108 is inserted into the anchor 102 (as described below), the anchor is fully seated against the rest of the inserter 106. The inserter 106 also has an elongated inner shaft 112 extending between a proximal end and a distal end of the inserter 106. The inner shaft 112 is dimensioned for receipt within the outer shaft 108 and is axially moveable independent of the outer shaft 108. FIG. 1B is an isometric view of the inserter 106, further illustrating the threads 110 on the inner surface of the distal end 124. The inserter 106, including the outer shaft 108 and inner shaft 106112, can be made from any type of metal or other suitable material.

Figure 2A:
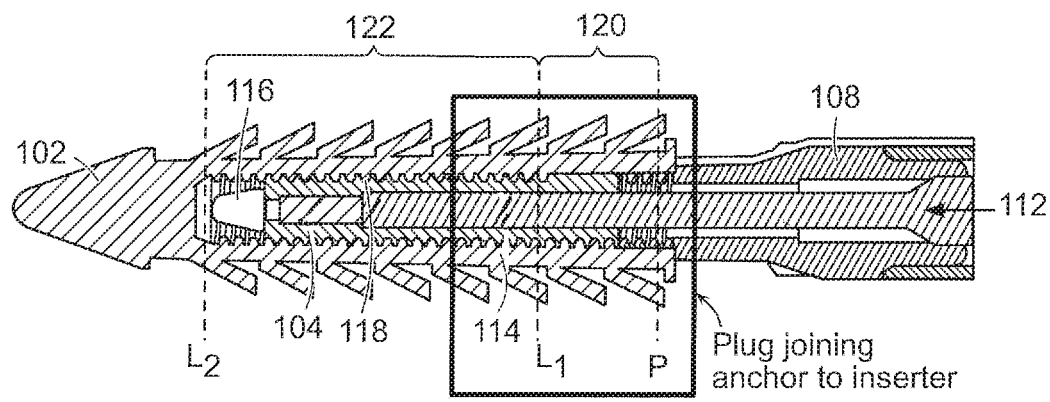
FIGS. 2A and 2B are illustrations of further examples of the suture anchor system of this disclosure.
Figure 2B:
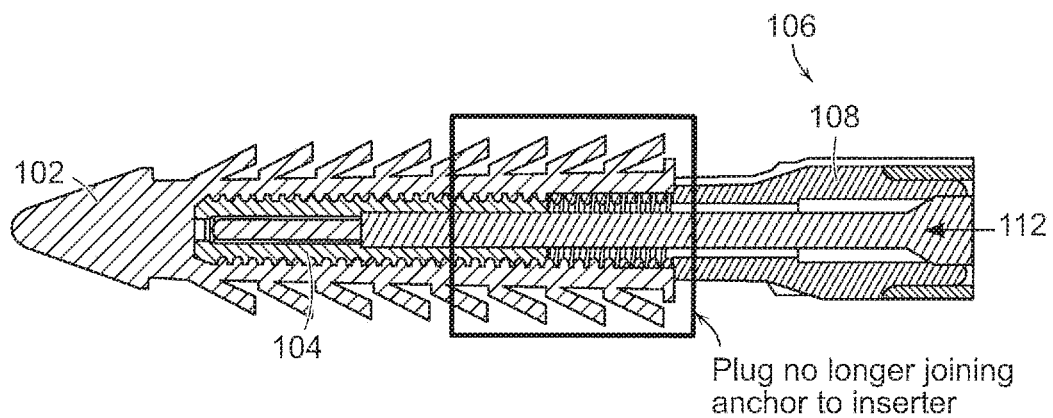

Referring now to FIGS. 2A and 2B, the suture anchor 102 includes an elongated anchor body 114 extending longitudinally between a proximal end and a closed distal end. The suture anchor 102 also has a closed eyelet 116, extending transversely through a longitudinal axis of the anchor 102, and dimensioned to receive one or more sutures (not shown). The anchor 102 further includes a suture anchor cannulation 118 formed within the anchor body 114 and intersecting the eyelet 116. The suture anchor cannulation 118 has a smooth-sided (e.g. non-threaded) proximal cannulation portion 120 extending distally from a proximal end (P) of the anchor body 114 to a first longitudinal position ($L_1$) proximal to the eyelet 116, and a threaded distal cannulation portion 122 extending distally from the first longitudinal position ($L_1$) to a second longitudinal position ($L_2$) distal to the eyelet 116. FIG. 2A shows the threaded plug 104 joining the anchor 102 to the inserter 106, as further described below. FIG. 2B shows the threaded plug 104 no longer joining the anchor 102 to the inserter 106, as further described below.

Figure 2C:
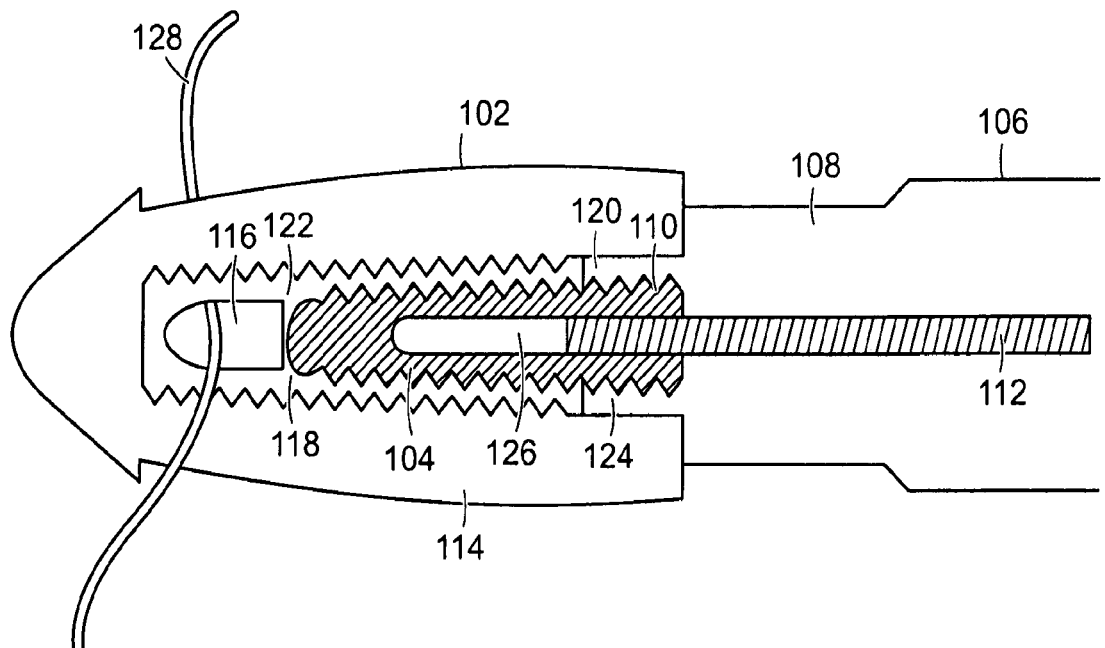
FIGS. 2C and 2D are illustrations of an example of the method of using the suture anchor system of this disclosure.

In use, as shown in FIG. 2C, the anchor 102 is mounted to the inserter 106 by means of the threaded plug 104, which is engaged with both the anchor 102 and the inserter 106, as described herein. A suture 128 may be first routed through the eyelet 116. The threaded distal end 124 of the outer shaft 108 of the inserter 106 is inserted within the proximal cannulation portion 120 of the anchor 102. The distal end of the threaded plug 104 is engaged with the distal cannulation portion 122 of the anchor 102 while the proximal end of the threaded plug 104 is engaged with the threads 110 of the distal end 124 of the outer shaft 108. This position defines a first axial position wherein the threaded plug 104 engages both the anchor body 114 and the outer shaft 108 of the inserter 106 and the distal terminus of the threaded plug 104 is proximal to the eyelet 116. So positioned, the threaded plug 104 advantageously secures the anchor 102 to the inserter 106 and also provides a bridge for transmission of force between the anchor 102 and inserter 106 during the anchor insertion process. In addition, this arrangement means that there is less opportunity for a surgeon to accidentally knock the anchor 102 off of the inserter 106. The surgeon will therefore be able to advance the suture anchor system 100 in and out of a surgical cannula more reliably.

Figure 2D:
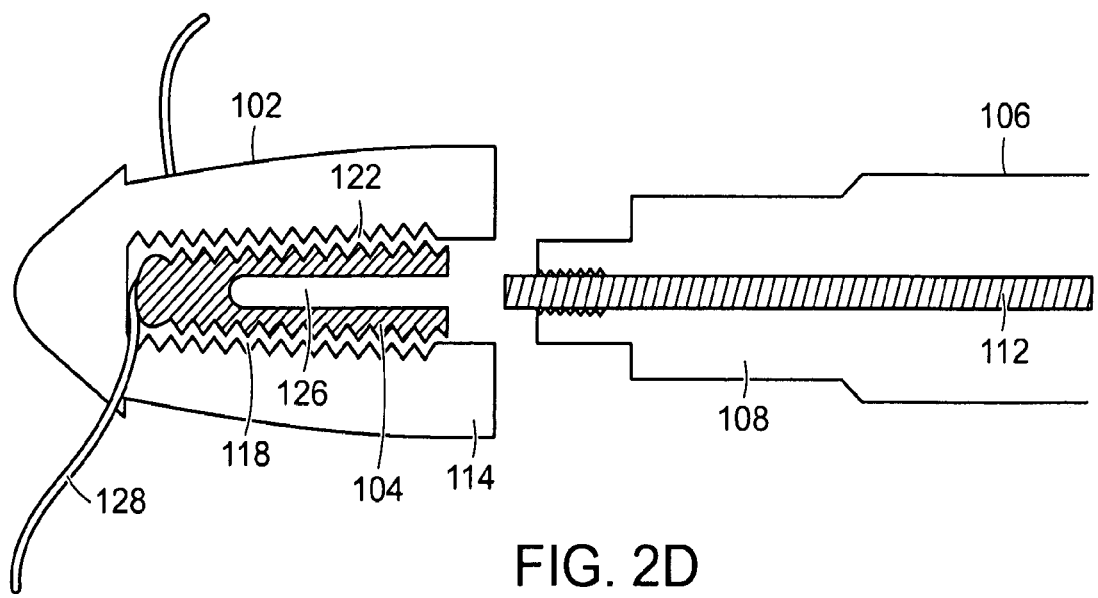

As shown in FIG. 2D, after insertion of the anchor 102 into a bone hole of a patient (not shown), the suture 128 is secured to the anchor 102, as described herein. The inner shaft 112 of the inserter 106 is distally advanced through the cannula 126 of the threaded plug 104 by rotation of the inner shaft 112 by a means of a part of a handle attached to the inserter 106 (not shown). Additional distal advancement of the inner shaft 112 to the distal end of the cannula 126 urges the threaded plug 104 distally into the distal cannulation portion 122. The suture 128 is then secured between a distal terminus of the threaded plug 104 and the distal terminus of the suture anchor cannulation 118. The distal advancement of the threaded plug 104 further positions the threaded plug 104 fully within the anchor 102 and unengaged with the inserter 106. This position defines a second axial position, wherein the threaded plug 104 engages the anchor body 114 but not the outer shaft 108 of the inserter 106, and the distal terminus of the threaded plug 104 abuts the distal terminus of the anchor body cannulation 118. Accordingly, the inserter 106 (both the inner shaft 112 and outer shaft 108) is fully retracted from the anchor 102, leaving the anchor 102, the threaded plug 104, and the suture 128 secured to the bone hole.

Figure 3:
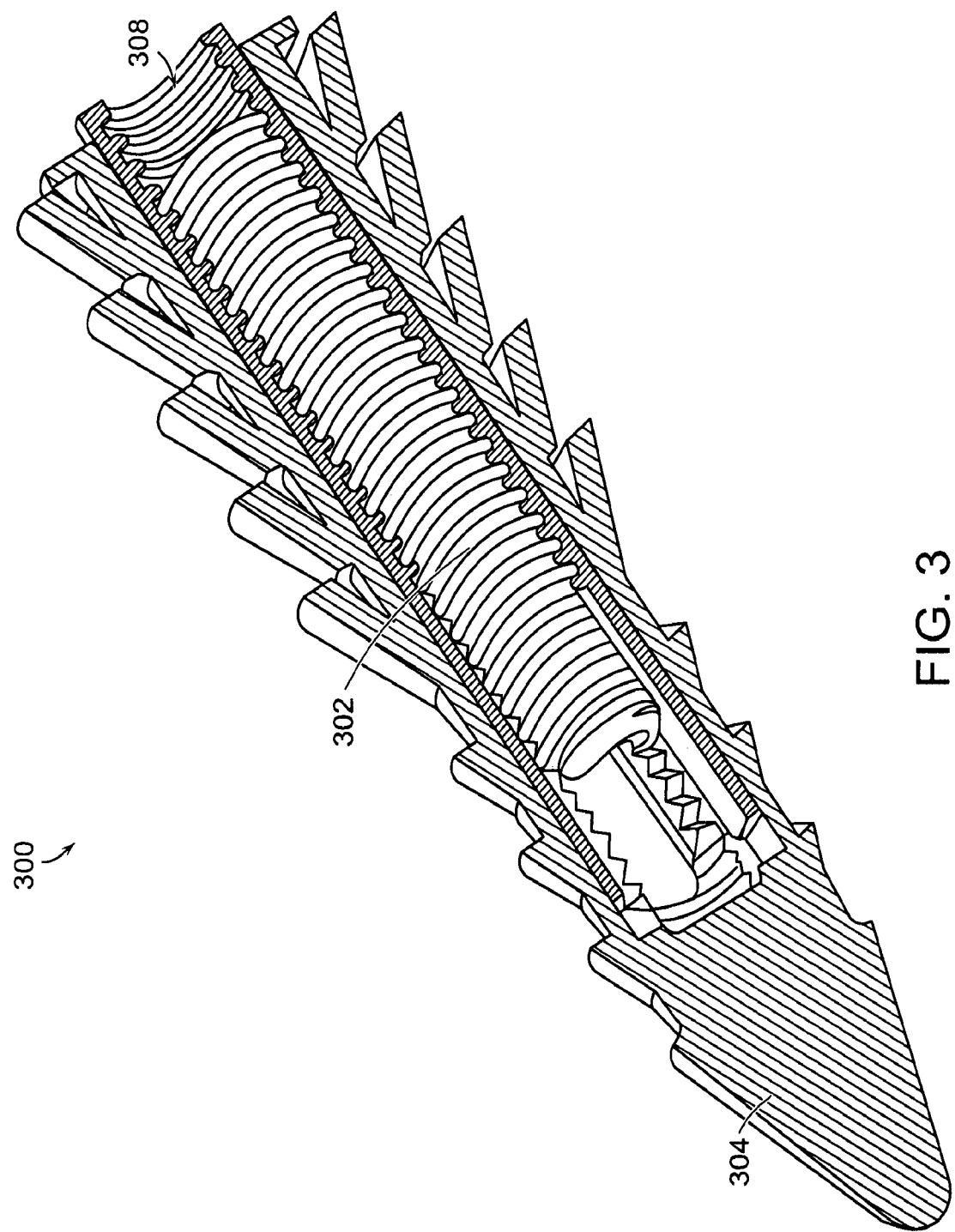
FIG. 3 is an alternative example of the suture anchor system of this disclosure.

FIG. 3 shows an alternative example of the suture anchor system of this disclosure. As shown in FIG. 3, the geometry of the anchor 304, the plug 302 and the outer shaft 308 can be manipulated to the point where the plug 302 can sit within the outer shaft 308, yet still perform the same function.

Although the invention has been described with respect to various embodiments, it should be realized this invention is also capable of a wide variety of further and other embodiments within the spirit and scope of the appended claims.

The invention claimed is:

1. A suture anchor system, comprising:
   an inserter comprising:
      an elongated, cannulated outer shaft, wherein a distal end of the outer shaft comprises internal threads; and
      an elongated inner shaft dimensioned for receipt within the outer shaft and axially moveable along the outer shaft; and
   an anchor, comprising:
      an eyelet, extending transversely through a longitudinal axis of the anchor dimensioned to receive one or more sutures; and
      a cannulation extending along the longitudinal axis of the anchor and intersecting the eyelet, the cannulation including a threaded portion; and
      a threaded, tubular plug comprising a longitudinal cannula; wherein the inner shaft of the inserter is engageable with the plug to move the plug distally with respect to the anchor from a first axial position to a second axial position; wherein, in the first axial position, the plug threadingly engages both the anchor and the internal threads of the outer shaft of the inserter and a distal terminus of the plug is proximal to the eyelet; and wherein, in the second axial position, the plug is advanced into the anchor so that the plug concomitantly threadingly disengages from the outer shaft of the inserter and secures a suture disposed through the eyelet between the plug and the anchor cannulation.

2. The suture anchor system of claim 1, wherein the anchor cannulation also includes a non-threaded portion.

3. The suture anchor system of claim 1, wherein a diameter of the distal end of the inserter is sized so as to fit within a proximal portion of the anchor such that the internal threads are also disposed within the proximal portion.

4. The suture anchor system of claim 1, wherein the distal end of the outer shaft is configured to couple with the anchor.

5. The suture anchor system of claim 1, wherein the anchor is comprised of a plastic, a bioabsorbable material or a metal.

6. The suture anchor system of claim 1, wherein the anchor has a closed distal end.

7. The suture anchor system of claim 1, wherein the plug has a distal non-threaded portion.

8. The suture anchor system of claim 1, wherein the inner shaft is configured to advance the plug distally with respect to the anchor by rotating.

9. The suture anchor system of claim 1, wherein the plug is comprised of any one of a plastic, a bioabsorbable material and a metal.

10. The suture anchor system of claim 1, wherein a length of the plug is between about 5 mm and about 8.5 mm.

11. The suture anchor system of claim 1, wherein a diameter of the plug is between about 1.9 mm and about 2.1 mm.

12. A method of securing a suture, comprising:
   routing a suture through an eyelet that extends transversely through a longitudinal axis of an anchor, the anchor comprising a cannulation and intersecting the eyelet, the cannulation including a threaded portion threadingly engaged with a distal end of a threaded, tubular plug; the threaded tubular plug directly threadingly engaged with a threaded distal end of a cannulation of an inserter outer shaft, the inserter further comprising an elongated inner shaft dimensioned for receipt within the outer shaft, and wherein the inner shaft is axially moveable relative to the outer shaft;
   engaging the inner shaft of the inserter with the plug and moving the plug distally with respect to the anchor from a first axial position to a second axial position; wherein, in the first axial position, the plug engages both the anchor body and the threaded distal end and a distal terminus of the plug is proximal to the eyelet; and wherein, while moving to the second axial position, the plug advances into the anchor, threadingly disengages from the inserter and also cover at least a portion of the eyelet so as to secure the suture between a distal terminus of the plug and distal terminus of the anchor cannulation.

13. The method of claim 12, further comprising removing the inserter.

14. The method of claim 12 further comprising the step of inserting the anchor at least partially into a target tissue while the plug is in the first axial position, the first axial position configured to aid in coupling the inserter to the anchor.

15. A suture anchor system, comprising:
an inserter having a first shaft with an internally threaded cavity extending from a distal end of the first shaft and an inner shaft coaxially disposed within the first shaft, and axially moveable relative to the first shaft; and
an anchor, including a distal tip portion and a proximal anchoring portion, an eyelet, extending transversely through a longitudinal axis of the distal tip portion, the eyelet dimensioned to receive one or more sutures; and wherein the anchor further comprises a lumen extending along a portion of the anchor and intersecting the eyelet, the lumen having a threaded portion; and
a plug having an externally threaded outer surface;
wherein the inner shaft of the inserter is configured to engage the plug and move the plug distally with respect to the anchor from a first axial position to a second axial position; wherein, in the first axial position, the plug externally threaded outer surface threadingly engages both the anchor and the threaded cavity of the first shaft and a distal terminus of the plug is proximal to the eyelet; and wherein in the second axial position, the plug is advanced into the anchor so as to threadingly disengage from the threaded cavity of the first shaft and secure the one or more sutures disposed through the eyelet between the plug and the anchor lumen.

16. The system of claim 15 wherein the first shaft is dimensioned for receipt within the proximal anchoring portion.

17. The system of claim 15 wherein the first axial position is configured to provide coupling and a force transmission bridge via the plug between the anchor and inserter during insertion of the anchor into a target tissue so as to gain linear stability without an additional suture wrapped though the anchor and cleated to the inserted handle.

18. The system of claim 15 wherein the second axial position is configured to both secure a length of suture with the anchor and release the inserter from the anchor.

19. A method of securing a suture, comprising:
routing a suture through an eyelet of an anchor, the eyelet extending transversely through a longitudinal axis of the anchor, the anchor further comprising a cannulation formed within the anchor and intersecting the eyelet, the cannulation including a threaded portion; and
inserting at least a portion of the anchor into a target tissue with an inserter, wherein while inserting, the anchor is coupled to the inserter via a plug that is directly threadingly engaged with both the anchor and an internally threaded cavity at a distal end of an outer shaft of the inserter;
advancing an inner shaft of the inserter coaxially disposed within the outer shaft and coupled to the plug, the advancing moving the plug so as to secure the suture with the anchor and disconnect the plug from the inserter.

20. The method of claim 19 wherein advancing the inner shaft moves the plug from a first axial position to a second axial position; wherein, in the first axial position a distal terminus of the plug is proximal to the eyelet and a proximal portion of the plug is threadingly engaged with the internally threaded cavity of the outer shaft; and wherein in the second axial position, the plug is threadingly disengaged from the threaded cavity of the outer shaft and a distal portion of the plug covers at least a portion of the eyelet.

* * * * *